US006956104B2

(12) United States Patent  
Seino et al.

(10) Patent No.: US 6,956,104 B2  
(45) Date of Patent: Oct. 18, 2005

(54) PROTEIN RIM2

(75) Inventors: Susumu Seino, Chiba (JP); Tadao Shibasaki, Chiba (JP); Nobuaki Ozaki, Nagoya (JP)

(73) Assignees: JCR Pharmaceuticals Co., Ltd., Hyogo (JP); Susumo Seino, Chiba (JP)

( * ) Notice: Subject to any disclaimer, the term of this patent is extended or adjusted under 35 U.S.C. 154(b) by 366 days.

(21) Appl. No.: 10/180,326

(22) Filed: Jun. 27, 2002

(65) Prior Publication Data

US 2003/0049661 A1 Mar. 13, 2003

Related U.S. Application Data

(62) Division of application No. 09/617,099, filed on Jul. 14, 2000, now Pat. No. 6,790,949.

(30) Foreign Application Priority Data

Oct. 8, 1999 (JP) ............................................ 11-288372

(51) Int. Cl.[7] ........................ C07K 14/00; A61K 38/00; C12N 15/00; C12P 21/04

(52) U.S. Cl. ...................... 530/350; 530/300; 435/69.7; 435/320.1; 435/440; 435/449; 536/23.5

(58) Field of Search ................................ 530/350, 300; 435/69.7, 320.1, 440, 449; 536/23.5

(56) References Cited

PUBLICATIONS

Rothman, J.E., *Mechanisms of Intracellular Protein Transport*, Nature, 372, 55–63 (1994).
Südhof, T.C., *The Synaptic Vesicle Cycle: A Cycle of Protein–Protein Interactions*, Nature, 375, 645–653 (1995).
Hawkins, R.D., et al., *Learning to Modulate Transmitter Release: Themes and Variations in Pynaptic Plasticity*, Annu. Rev. Nuerosci., 16, 625–665 (1993).
Lonart, G., et al., *Mechanisms of Action of rab3A in Mossy Fiber LTP*, Neuron, 21, 1141–1150 (1998).
Renström, E., et al., *Protein Kinase A–Dependent and Independent Stimulation of Exocytosis by cAMP in Mouse Pancreatic B–Cells*, J. Physiology, 502.1, 105–118, (1997).
Yoshimura, K., et al., *Cyclic AMP Potentiates Substance P–Induced Amaylase Secretion by Augmenting the Effect of Calcium in the Rat Parotid Acinar Cells*, Biochemica et Biophysica Acta, 1402, 171–187 (1998).
De Rooij, J., et al. , *Epac is a Rap1 Guanine–Nucleotide–Exchange Factor Directly Activated by Cyclic AMP*, Nature, 396, 474–477 (1998).
Kawasaki, H., et al., *A Family of cAMP–Binding Proteins that Directly Activate Rap1*, Science, 282, 2275–2279 (1998).
Wang, Y., et al., *Rim is a Putative Rab3 Effector in Regulating Synaptic–Vesicle Fusion*, Nature, 388, 593–598 (1997).

*Mutagenesis of Cloned DNA*, Current Protocols in Molecular Biology, vol. 1, Chapter 8, 8.0.1–8.5.10 (1997).
*Expression Vectors*, Catalog of Vectors, BIOS Scientific Publishers Ltd., 9–12 (1994).
*Introduction of Plasmid DNA into Cells*, Current Protocols in Molecular Biology, vol. 1, Unit 1.8, 1.8.1–1.8.10 (1997).
*Introduction of DNA into Mammalian Cells*, Current Protocols in Molecular Biology, vol. 1, Chapter 9, 9.0.1–9.8.2 (1997).
*Transduction of Genes Using Retrovirus Vectors*, Current Protocols in Molecular Biology, vol. 1, Unit 9.9, 9.9.1–9.17.3 (1996).
*Immunology*, Current Protocols in Molecular Biology, vol. 1, Chapter 11, 11.0.1–11.16.13 (1997).
Prentki, M. and Matschinsky, F.M., $Ca^{2+}$, *cAMP, and Phaspholipid–Derived Messengers in Coupling Mechanisms of Insulin Secretion*, Phys. Reviews, 67, 4, 1185–1248 (1987).
Shirataki, H., et al., *Rabphilin–3A, a Putative Target Protein for smg p25A/rab3A p25 Small GTB–Binding Protein Related to Synaptotagmin*, Mol. Cell. Biol., 13, 4, 2061–2068 (1003).
Li, C., et al., *Synaptic Targeting of Rabphilin–3A, a Synaptic Vesicle $Ca^{2+}$/Phospholipid–Binding Protein, Depends on rab3A/3C*, Neuron, 13, 885–898 (1994).
Kotake, K., et al., *Noc2, a Putative Zinc Finger Protein Involved in Exocytosi in Endocrine Cells*, J. Biol. Chem., 272, 47, 29407–29410 (1997).
Steinberg, R.A., et al., *Activation of Type 1 Cyclic AMP–Dependent Protein Kinases with Defective Cyclic AMP–Binding Sites*, J. Biol. Chem., 262, 6, 2664–2671, (1987).
Tanaka, J., et al., *Cellular Distribution of the P2X, ATP, Receptor mRNA in the Brain and Non–Neuronal Organs of Rats*, Arch. Histol. Cytol., 59, 485–490 (1996).
Jones, P.M. and Persaud, S.J., *Protein Kinases, Protein Phosphorylation, and the Regulation of Insulin Secretion from Pancreatic β–Cells*, Endocrine Rev., vol. 19, 429–461 (1998).
Inagaki, N. et al., *Cloning and Functional Characterization of a Third Pituitary Adenylate Cyclase–Activating Polypeptide Receptor Subtype Expressed in Insulin–Secreting Cells*, Proc. Nat. Acad. Sci., 91, 2679–2683 (1994).

(Continued)

Primary Examiner—Jon Weber  
Assistant Examiner—Rita Mitra  
(74) Attorney, Agent, or Firm—Greenblum & Bernstein, P.L.C.

(57) ABSTRACT

Provided is a protein used in the development of a therapeutic agent for neuron- or endocrine cell-related diseases, in which the transport system is involved. The protein has an amino acid sequence with one or more amino acids deleted, substituted, inserted or added relative to the amino acid sequence set forth under SEQ ID NO:1 in the Sequence Listing and which has a property to interact with GDP/GTP exchange factor II.

2 Claims, 8 Drawing Sheets

OTHER PUBLICATIONS

Gonoi, T. et al., *Functional Neuronal Ionotropic Glutamate Receptors are Expressed in the Non–Neuronal Cell Line MIN6*, J. Biol. Chem., vol. 269, No. 25, 169898–169925, (1994).

Wang et al. "Rattus norvegicus RIM2mRNA, complete cds", Database GenEmbl, Accession NO: AF199322, Jul. 4, 2000.

Wang et al. "RIM2", Database SPTREMBL_16, Accession No: Q9J1S1, Oct. 1, 2000.

Wang, Y., et al., *Rim is a putative Rab3 effector in regulating synaptic–vesuicle fusion*, Nature, vol. 388, 593–598 (1997).

Database Swall 'Online!', Andersson, B., et al., *Hypothetical 41.8 Kda Protein(Fragment)*, retrieved from EBI, Database accession No. 043413 (1998).

Database EMBL 'Online!', Ohara, O., et al., *Homo Sapiens mRNA for KIAA0751 protein, complete cds*, retrieved from EBI, Accession No. AB018294 (1998).

Ozaki, N., et al., *cAMP–GEFII is a direct target of cAMP in regulated exocytosis*, Nature Cell Biology, vol. 2, 805–811 (2000).

Wang, Y., et al., *The RIM/NIM Family of Neuronal C2 Domain Proteins*, JBC, vol. 275, No. 26, 20033–20044 (2000).-

Figure 1

```
cAMP-A  QDIGTNWYAVLA SLDVKVSETSSHQDAVTICTLGIGTAF SIL-DNTP H TIVTR  130
cAMP-B  QEEGTSWYIILK SVNV-VIYGKG---V-VCTLHEGDDF KLALVNDAF A SIVLR  439
RIα-A   QDEGDNPYVIDQ EMDVYVNNEWAT-----SVGEGGSF ALIYGTP A TVKAK  218
RIα-B   QEPGDEFFIILE TAAV-LQRRSENEEPVEVGRLGPSDYF IALLMNRP A TVVAR  342
```

PROTEIN RIM2

This application is a divisional of application Ser. No. 09/617,099, filed Jul. 14, 2000, now U.S. Pat. No. 6,790,949 which claims priority of Japanese Application No. 11-288372, filed Oct. 8, 1999. The entire disclosure of application Ser. No. 09/617,099 is expressly incorporated by reference herein in its entirety.

FIELD OF THE INVENTION

The present invention relates to protein Rim2, which is a novel isoform of Rim, i.e., a protein that interacts with a low molecular G protein Rab3 and is proposed to serve as a regulator of Rab3-dependent synaptic vesicle fusion, and which specifically interacts with the GDP/GTP exchange factor (GEFII; a cAMP sensor). More specifically, the present invention relates to elucidation of the mechanisms of intracellular vesicle transport and secretion, and to the novel protein Rim2 which is useful in diagnosis of endocrine-related diseases or neuropathy and in development of agents for prevention and treatment thereof, the gene encoding Rim2 and an antibody addressed to Rim2 protein.

Rim2 is considered to be a regulatory factor of vesicle fusion. It was found in the course of the present invention that the protein is expressed predominantly in endocrine tissues and endocrine- and neuroendocrine-derived cell lines. GTP-Rab3/GEFII/Rim complex is thought to participate in the regulation of exocytosis of neurons and endocrine cells, in a cAMP-dependent and protein kinase A (PKA) independent manner.

BACKGROUND OF THE INVENTION

Transport of substances between cell organelles, which are unit membrane-enclosed structures such as endoplasmic reticulum, is conducted by intracellular vesicle transport. In endocrine cells including pancreatic β-cells and pituitary cells, peptides/proteins synthesized at ribosomes are received by the endoplasmic reticulum, from which they are transported in vesicles, which are transformed into secretory vesicles through the Golgi body and transported to the cell membrane, where they are released out of the cell via a step which includes fusion of the membranes. In neurons, neurotransmitter-containing precursors of synaptic vesicles are formed in Golgi bodies and transported by microtubules along the axon and stored at the synapse. Depolarization of the pre-synaptic membrane causes the vesicles to fuse with the pre-synaptic membrane and thus the neurotransmitters are released. This type of secretion based on the fusion of the vesicles and the cell membrane is called exocytosis.

In contrast, when extracellular substances such as hormones including cell growth factors are bound to the cell membrane, the complexes thus formed are invaginated into the cell to form endosomes. This type of uptake of environmental substances is called endocytosis.

Formation of vesicles, such as by budding, commonly observed both in exocytosis and endocytosis, and docking and fusion, the phenomena observed in process of their transportation and binding to other membrane systems, are regulated by a GTP-binding, low-molecular protein, called G protein. More than 30 types of this protein are known. The group of the proteins, which are also classified in Rab family, regulate the intracellular vesicle transport system.

With regard to the intracellular vesicle transport system, it is understood today that a cell is in a resting state when Rab protein occurs in a bound form to guanine nucleotide diphosphate (GDP), and that budding, docking and fusion are triggered as a result of a process in which a protein having GEF activity act on Rab protein and converts it to GTP-binding Rab protein, to which GTP binds to form a GTP-Rab complex, which in turn binds to a corresponding target protein on the membrane.

Stimulus-secretion coupling plays an important role in exocytosis observed in many cell types including neurons and endocrine cells [J. E. Rothman, Nature 372:55(1994); T. C. Sudhof, Nature 375:645 (1995)]. While a rise in intracellular $Ca^{2+}$ concentration is important in the regulation of exocytosis, other signals are also known to play important roles. cAMP (cyclic adenosine-3',5'-monophosphate)/PKA (cAMP-dependent protein kinase A) signaling pathway is known to regulate exocytosis in many of neurons, neuroendocrine cells and endocrine cells. In particular, cAMP has been thought to mediate long-term potentiation by increasing neurotransmitter release in the brain [R. D. Hawkins et al. Ann. Rev. Neurosci. 16:625(1993); G. Lonart et al., Neuron 21:1141(1998)]. cAMP also regulates exocytosis responsible for insulin release from pancreatic β-cells and amylase release from parotid acinar cells [P. M. Jones and S. J., Persaud, Endocrine. Rev. 19:429(1998); E. Renstrom, et al., J. Physiol. 502:105(1997); K. Yoshimura, Biochim. Biophys. Acta 1402:171(1998)].

In addition to its role in PKA-dependent phosphorylation of regulatory proteins associated with the process of exocytosis, it is known that cAMP also acts directly on the exocytotic machinery in neurons and non-neuronal cells [G. Lonart et al., Neuron 21:1141 (1998); E. Renstrom et al., J. Physiol. 502:105 (1997); K. Yoshimura, Biochim. Biophys. Acta, 1402:171(1998)].

During the search by the yeast two-hybrid screen (i.e., a method for detection of the interaction between two proteins in yeast cells) for an intracellular signaling molecule directly coupling to a sulphonylurea receptor, a component of pancreatic β-cell ATP-sensitive $K^+$ ($K_{ATP}$) channels [N. Inagaki et al. Proc. Natl. Acad. Sci. U.S.A. 91,2679 (1994)], a cAMP sensor protein (called "CAMPS") was identified and it was found that the protein has two putative cAMP binding domains, a Pleckstrin homology domain (PH domain), and a guanine nucleotide exchange factor (GEF) homology domain.

In the course of this study, two study groups independently reported cAMP binding proteins that activate Rap1, a member of the small G binding proteins [J. de Rooiji et al. Nature 396:474 (1998); H. Kawasaki et al. Science 282:2275 (1998)], and CAMPS was incidentally revealed to be a mouse homologue of cAMP-GEFII [H. Kawasaki et al. Science 282:2275 (1998)].

Though the mechanisms of intracellular vesicle transport system have thus gradually been clarified, substantial part of them remains still unknown. Further progress is needed for the understanding of the mechanisms so as to provide diagnostic agents or therapeutics for a variety of diseases which involve neurons or endocrine cells.

Unlike the former suggestion that only a single cAMP binding domain was present in cAMP-GEFII, the study by the present inventors suggested the presence of two putative cAMP binding domains (cAMP-A and cAMP-B), based on a sequence alignment of cAMP-GEFII sequence and regulatory subunits of PKA. FIG. 1 shows the sequence alignment of the cAMP binding domains. The cAMP binding domains A and B (cAMP-A and cAMP-B, respectively) of cAMP-GEFII and the cAMP binding domains A and B of the PKA regulatory subunit I α (RI α-A and RI α-B, respectively) are shown. The invariant residues in the different cAMP-binding domains are indicated by black boxes.

As shown in FIG. 2, a glutathione-S-transferase (GST)-cAMP-A fusion protein bound to [$^3$H]cAMP with a dissociation constant (Kd) of ~10 μM, while the binding of [$^3$H]cAMP to a GST-cAMP-B fusion protein was not evident under the same conditions.

FIG. 2 shows the binding of cAMP to cAMP-A. GST-cAMP-A (filled circles) or GST-PKA RI α (open circles) was incubated with different concentrations of [$^3$H]cAMP (0–50 μM). The data for cAMP-A or PKA RI α are normalized relative to maximal cAMP binding activities. Kd values are 10.0±2.3 μM and 23.7±0.6 nM for cAMP and PKA RI α, respectively.

In the cAMP-B domain, the amino acid residue 423, which originally is glutamic acid (Glu), is substituted with lysine (Lys). This glutamic acid residue is important for cAMP binding. Considering that a more rapid dissociation than the wild-type was observed with a PKA regulatory subunit having an equivalent mutation (E-200-K), cAMP-B may also dissociate cAMP rapidly. Thus, a possibility remains that cAMP binds to the cAMP-B domain.

SUMMARY OF THE INVENTION

As identification of a target molecule of CAMPUS, cAMP-GEFII, would serve to show its physiological role, the present inventors attempted to find a molecule that interacts with cAMP-GEFII by means of a yeast two-hybrid screen (YTH) method on the MIN6 cDNA library (See "Identification of Interacting molecules by YTH Method").

Surprisingly, the present inventors found that cAMP-GEFII interacts with a novel isoform (named "Rim2" by the present inventors) of Rim (a molecule which specifically interacts with Rab3: Rab3-interacting molecule: Hereinafter referred to as "Rim1"). Rim1 protein is a putative effector of the small G protein Rab3 and is proposed to serve as a Rab3-dependent regulator of synaptic vesicle fusion [Y. Wang et al. Nature 388:593(1997)].

The full-length novel protein Rim2 sequenced by the present inventors, which consists of 1590 amino acid residues, was found to have 61.6% identity with rat Rim1. As FIG. 3 shows, a zinc finger, PDZ and two C2 domains were found highly conserved between Rim1 and Rim2.

Based on the above findings, the present invention provides a protein having the amino acid sequence set forth under SEQ ID NO:1 in the Sequence Listing.

The present invention further provides a protein having an amino acid sequence with one or more amino acids deleted, substituted, inserted or added relative to the amino acid sequence set forth under SEQ ID NO:1 in the Sequence Listing and which has a property to interact with GDP/GTP exchange factor II.

The present invention further provides a mouse gene which encodes the following proteins (1) or (2):
(1) a protein having the amino acid sequence set forth under SEQ ID NO:1 in the Sequence Listing,
(2) a protein having an amino acid sequence with one or more amino acids deleted, substituted, inserted or added relative to the above-identified amino acid sequence and which has a property to interact with GDP/GTP exchange factor II.

In the present specification, "one or more" amino acid residues are generally several (e.g., 3 or 4) to 10 residues.

The present invention further provides a DNA having a nucleotide sequence set forth under SEQ ID NO:2 in the Sequence Listing, the DNA being a cDNA corresponding to the above protein having the amino acid sequence set forth under SEQ ID NO:1 in the Sequence Listing.

The present invention further provides a DNA having a nucleotide sequence with one or more nucleotides deleted, substituted, inserted or added relative to the nucleotide sequence set forth under SEQ ID NO:2 in the Sequence Listing and encoding any one of the above proteins. Herein, "one or more" nucleotides are generally several (e.g., 3 or 4) to 10 nucleotides. A variety of such nucleotide sequences with one or more nucleotides deleted, substituted, inserted or added can be readily prepared by those skilled in the art by making use of the familiar knowledge on degeneracy of the genetic code.

The present invention further provides a DNA having the nucleotide sequence of the coding region of the any one of the above DNA's or of a DNA having the nucleotide sequence set forth under SEQ ID NO:2 in the Sequence Listing.

The present invention further provides a DNA fragment consisting of a part of any one of the above DNA's.

The present invention further provides a probe comprising a DNA which hybridizes with the DNA consisting of any one of the above nucleotide sequences.

The present invention further provides a primer DNA fragment consisting of a partial sequence of any one of the above nucleotide sequences.

The present invention further provides a recombinant vector having any one of the above DNA's.

The present invention further provides a monoclonal or polyclonal antibody directed to any one of the above proteins.

The present invention further provides a diagnostic agent for human use comprising any one of the above probes or antibodies. The diagnostic agent is useful in the test for such diseases as secretion disorders in secretory systems including pituitary, hypothalamus, pancreatic β-cells and parotid gland, or the test for brain-nervous system diseases.

The present invention further provides a therapeutic agent for any one of the above diseases.

BRIEF DESCRIPTION OF THE FIGURES

FIG. 1 illustrates a sequence alignment of the cAMP binding domains.

DETAILED DESCRIPTION OF THE INVENTION

Figure 2:
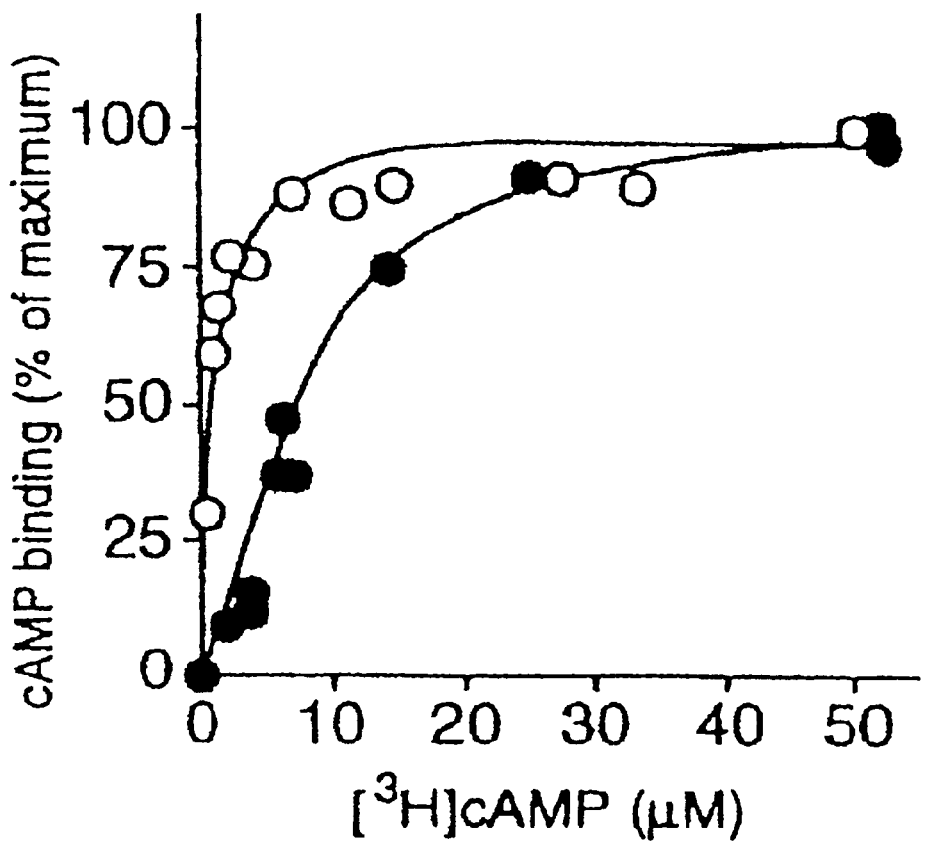
FIG. 2 is a graph showing the binding of cAMP to cAMP-A.
Figure 3:
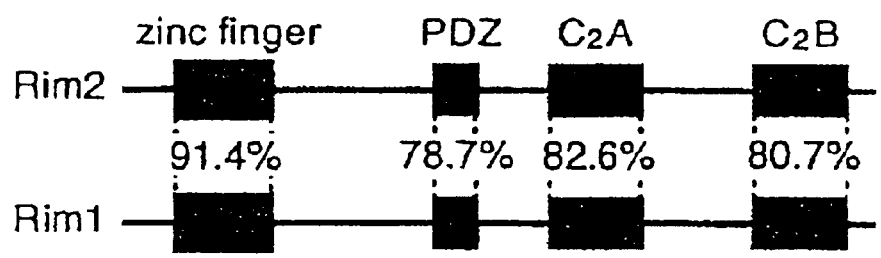
FIG. 3 illustrates a comparison of amino acid identity between Rim1 and Rim2, in zinc finger, PDZ and C2 domains.

A variety of mutants can be provided by means of recombinant DNA technology. First, mutations can be introduced into a DNA clone fragment through different chemical and/or enzymatic processes, and the mutant DNA's thus obtained are then sequenced to select particular mutants with intended merits. This method allows a systematic preparation of different mutants regardless of their phenotypes. General methods of preparing a mutant clone DNA are as follows.

1. With the help of an oligonucleotide, substitution, deletion, insertion or addition can be directly effected in a given DNA sequence. This method enables to introduce a number of mutations in a small region of a given DNA.

2. By using longer oligonucleotides, it is possible to synthesize a desired gene.

3. By means of region-specific mutagenesis, a desired mutation can be introduced into a large (1–3 kb) DNA region.

4. Linker-scanning mutagenesis of DNA is a method suited for introducing a cluster point mutation into a relatively small (4–10 bp) DNA region.

5. PCR is also utilized as a method for direct introduction of a mutation.

[References: Current Protocols in Molecular Biology., 3 Vols., Edited by Ausubel F. M. et al., John Wiley & Sons, Inc., Current Protocols., Vol. 1, Chapter 8: Mutagenesis of Cloned DNA, pages 8.0.1–8.5.10]

Also well known to those skilled in the art are methods of preparing plasmids or vectors which can express a desired gene including different mutations obtained by the above methods. That is, by inserting a DNA carrying a desired gene into a expression vector DNA using a combination of restriction enzymes and a ligase, a recombinant plasmid is readily constructed which carries the desired gene. The recombinant plasmid thus obtained is then introduced into different cells to transfect them, thereby producing transformed cells. Cells which may be utilized range from prokaryotes, e.g. *E. coli,* to yeast, insect, plant and animal cells.

[References: Vectors Essential Data. Gacesa P. and Ramji D. P., 166 pages. BIOS Scientific Publishers Limited 1994., John Wiley & Sons in association with BIOS Scientific Publishers Ltd. Expression vectors, pages 9–12.]

Introduction of a recombinant plasmid into host cells is effected by calcium chloride method or electroporation. Calcium chloride method provides efficient transformation without requiring any special apparatus. For higher efficiency, electroporation is recommended.

[References: Current Protocols in Molecular Biology, 3 Vols. Edited by Ausbel F. M. et al., John Wiley & Sons, Inc., Current Protocols, Vol. 1, unit 1.8: Introduction of Plasmid DNA into Cells, pages 1.8.1–1.8.10]

Two types are known of transfection generally carried out on animal cell lines, i.e., transient and permanent types. In transient transfection, transformed cells are cultured for 1–4 days to effect transcription and replication of the transfected gene, and then the cells are harvested and their DNA analyzed. Alternatively, in many studies, a stable transformant cell line is produced, in which the transfected gene is incorporated into the chromosomes. Examples of the method for transfection include calcium phosphate method, electroporation, and liposome fusion method.

[Reference: Current protocols in molecular biology. 3 vols. Edited by Ausubel F. M. et al., John Wiley & Son, Inc., Current Protocols. Vol. 1, chapter 9: Introduction of DNA into mammalian cells, pages 9.0.1–9.17.3.]

Polyclonal and monoclonal antibodies directed to the proteins (polypeptides) coded by Rim2 gene of the present invention or their fragments and analogues as well, are readily prepared using techniques well known in the art. Antibodies obtained may be used as laboratory reagents and diagnostic agents for diseases associated with Rim2 gene. The antibodies obtained are also used for preparation of antibody columns, for immunoprecipitation as well as for identification of the antigen by Western blotting.

A general method for preparing a monoclonal antibody in mg-scale directed to the proteins coded for by Rim2 gene of the present invention is as follows: Mice are inoculated with the antigen protein to immunize. The spleen is removed from the mice exhibiting a sufficient antibody titer. The spleen cells are dissociated, and selected B cells are fused with myeloma cells of B cell origin to form hybridoma cells which secrete the antibody. The monoclonal antibody secreted from the hybridoma cells is purified from the culture medium using an affinity column, ion-exchange, or gel filtration, etc. The polyclonal antibody of the present invention may be prepared by a conventional method: Using rabbits, horses, mice or guinea pigs as immunized animals, the antigen protein is inoculated along one of the schedules known in the art to immunize the animals, and then IgG, etc. are isolated from the collected serum.

[Reference: Current protocols in molecular biology, 3 vols. Edited by Ausubel F. M. et al., John Wiley & Sons, Inc., Current Protocols, Vol. 2, chapter 11: Immunology, pages 11.0.1–11.16.13.]

In order to assess the specificity of interaction between cAMP-GEFII and Rim2, the present inventors evaluated the binding of a FLAG-tagged cAMP-GEFII protein to a GST-Rim2 fusion protein immobilized on glutathione beads (See "Study on Interaction between Rim2 and cAMP-GEFII: I").

Figure 4:
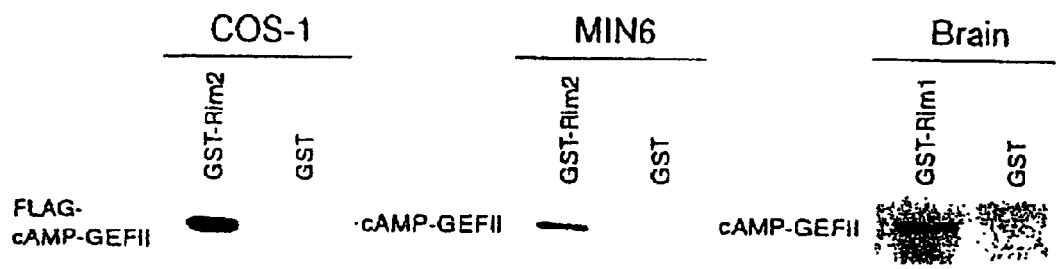
FIG. 4 shows the results of immunoblotting showing the interaction between cAMP-GEFII and Rim1 or Rim2.

Briefly, lysates from COS-1 cells transfected with FLAG-tagged cAMP-GEFII, from MIN6 cells or from mouse brain homogenate were evaluated for binding to GST-Rim1, GST-Rim2 or GST alone. cAMP was detected by immunoblotting with an anti-FLAG antibody (FIG. 4, left) or an anti-cAMP-GEFII antibody (FIG. 4, center and right), respectively. These results demonstrates that cAMP-GEFII protein interacts with GST-Rim2 protein. Likewise, GST-Rim1 protein also bound to cAMP-GEFII in the mouse brain homogenate (See "Study on Interaction between Rim1 and cAMP-GEFII") (FIG. 4, right). These results confirms that cAMP-GEFII interacts with Rim 1 and Rim2.

Figure 5:
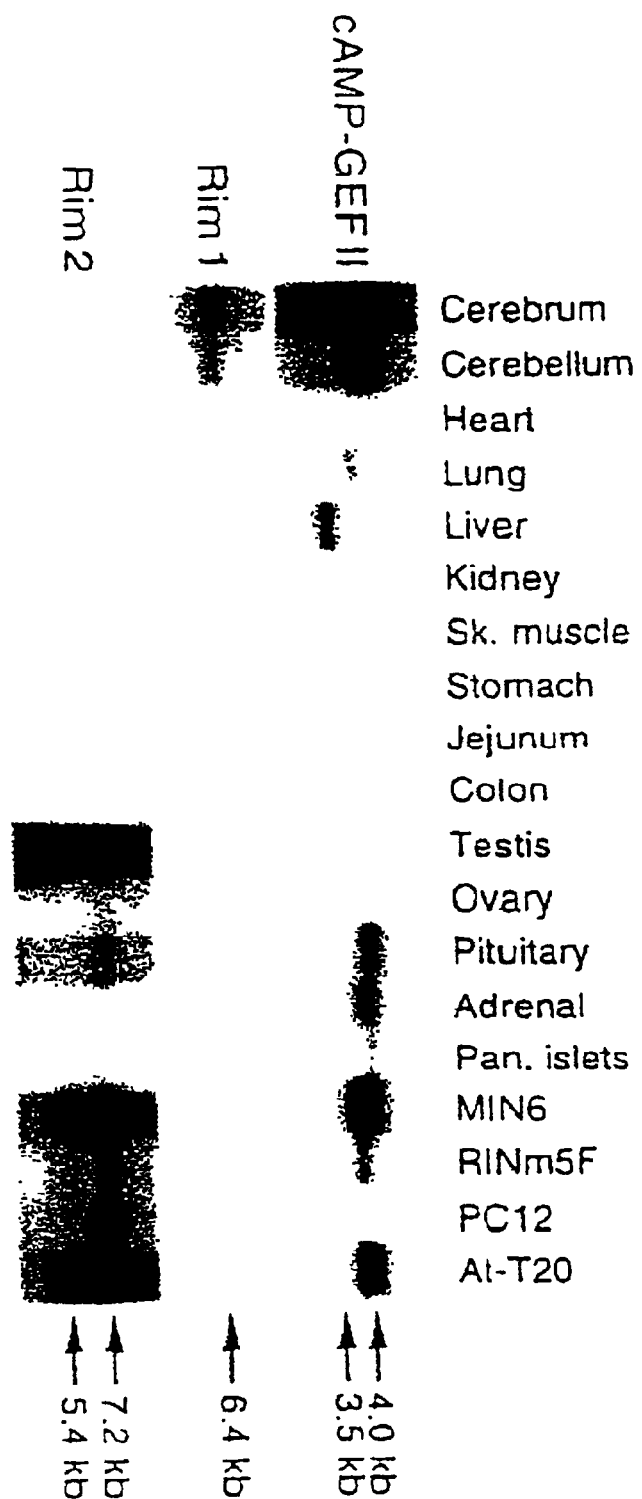
FIG. 5 shows the results of Northern blot analysis of cAMP-GEFII, Rim1 and Rim2 in various rat tissues and endocrine- and neuroendocrine-derived cell lines.

FIG. 5 shows the results of the northern blot analyses of cAMP-GEFII, Rim1 and Rim2 in various rat tissues and endocrine- and neuroendocrine-derived cell lines (See "Northern Blotting in Rat Tissues"). Ten $\mu$g samples of total RNA from various tissues and cell lines (except 5 $\mu$g for pancreatic islets) were used. Hybridization and washing were performed under standard conditions. The faint signals seen in Rim2 mRNA blot analysis of cerebrum and cerebellum are due to cross-hybridization with the Rim1 cDNA probe used. FIG. 5 shows that Rim2 mRNA is expressed predominantly in endocrine tissues and endocrine- and neuroendocrine-derived cell lines, including pituitary, pancreatic Langerhans' islet cells, MIN6 cells, and PC12 cells.

Rim2 mRNA was detected in the brain by reverse transcriptase-PCR (data not shown). Rim1 mRNA, in contrast, was found to be expressed in cerebrum, cerebellum, and pituitary by a similar analysis.

Figure 6:
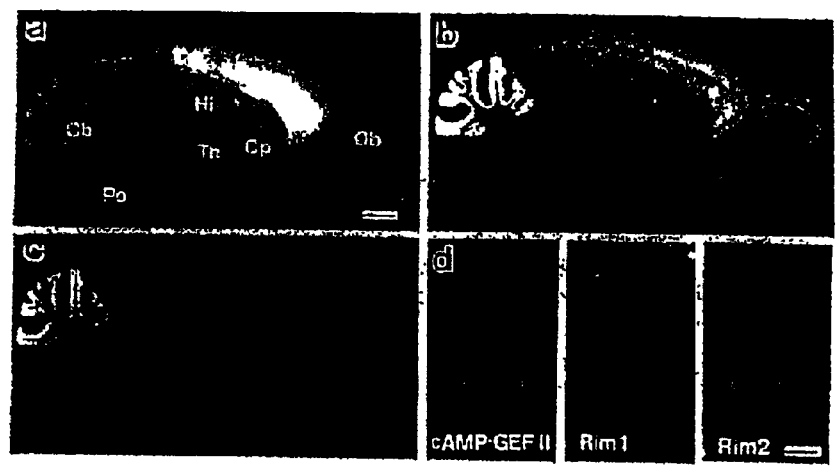
FIG. 6 is the result of In situ hybridization showing the localization of Rim1 and Rim2 in mouse brain and pituitary.

The major transcripts for Rim1 and Rim2 have 6.4 kb for Rim1, and 7.2 kb and 5.4 kb for Rim2. There are also found several minor transcripts, which occur due probably to alternative splicing.

cAMP-GEFII mRNA is generally coexpressed with Rim1 or Rim2 mRNA in tissues and cell lines in which regulated exocytosis is known to occur. FIG. 6 illustrates the results of in situ hybridization showing the localization of Rim1 and Rim2 in mouse brain and pituitary. In the figure: (a) cAMP-GEFII; (b) Rim1; (c) Rim2; (d) pituitary. The scale bar corresponds to 1 mm. Abbreviations: Cb=cerebellum, Cp=caudoputamen, Cx=cortex, Hi=hippocampus, Ob=olfactory bulb, Po=pons, Th=thalamus Rim2 mRNA is found expressed only in the cerebellar cortex, while Rim1 mRNA is expressed in cerebral cortex, hippocampus (especially CA3 and dentate gyrus), olfactory bulb, and cerebellar cortex (See "In situ Hybridization in Mouse Brain"). The distribution of cAMP-GEFII mRNA overlaps largely with that of Rim1 mRNA in the brain. It is confirmed that Rim2 mRNA and cAMP-GEFII mRNA are coexpressed in anterior pituitary.

Figure 7:
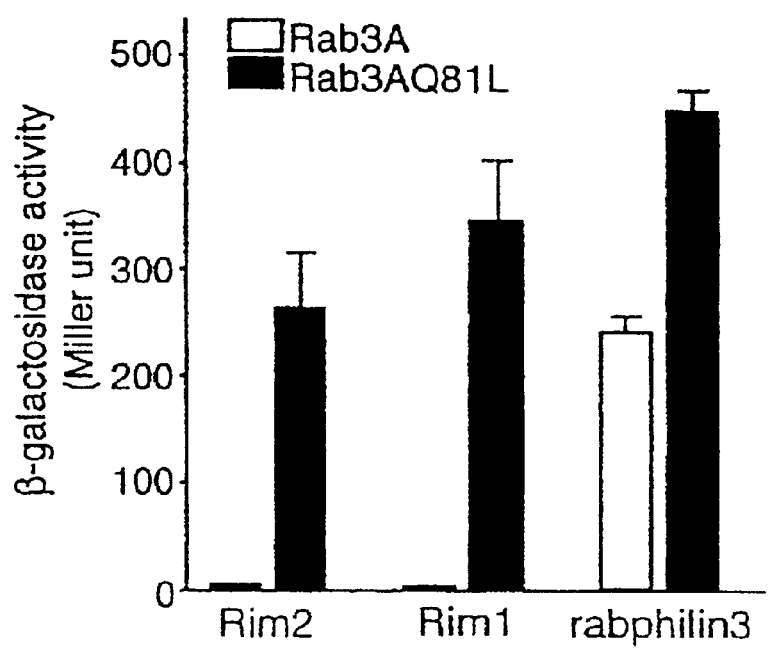
FIG. 7 is a graph showing the result of yeast two-hybrid assays.

Rim1 is proposed to be a Rab3 effector, a low molecular weight G protein [Y. Wang, et al., Nature 388,593 (1997)]. Using yeast two-hybrid assays (See "Study on Interaction between Rim2 and Rab3A".), the present inventors found that Rim2, like Rim1, interacts with active Rab3A (Q81L) (FIG. 7). FIG. 7 shows the results of the yeast two-hybrid assays. Rim1, Rim2 or rabphilin3 and wild-type Rab3A or constitutively active Rab3A (Q81L) in various combinations were determined by transactivation of liquid β-galactosidase activity.

Figure 8:
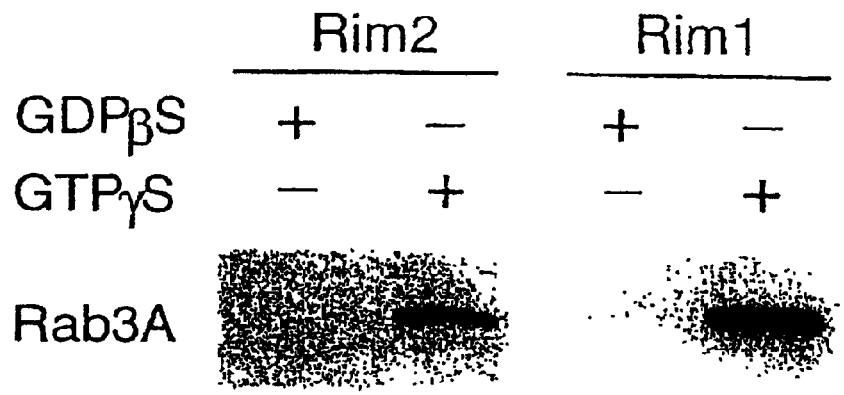
FIG. 8 illustrates the result of immunoblotting showing the interaction between Rab3A and Rim1 or Rim2 in vitro.

In addition, the immobilized GST-Rim2 bound only to the GTPγS-bound form of Rab3A (FIG. 8). FIG. 8 shows the interaction between Rab3A and Rim1 or Rim2 in vitro, which is the result obtained by incubating GTPγS- or GDP γS-bound form of Rab3A with GST-Rim1 (residues 1–201) and GST-Rim2 (residues 1–345) immobilized on glutathione beads, respectively. Rab3A was detected by immunoblotting with anti-Rab3A antibody. These results indicate that Rim2, like Rim1, binds to the GTP-activated form of Rab3A.

The interaction of cAMP-GEFII and Rim2 protein strongly suggests that cAMP-GEFII is involved in regulated-exocytosis. To determine its functional role, the present inventors examined the effect of cAMP on $Ca^{2+}$-dependent secretion in PC12 cells cotransfected with growth hormone (GH) and cAMP-GEFII (See "Study on GH secretion from Transfected PC12 Cells").

Since PC12 cells endogenously express Rim2 but not cAMP-GEFII, the exogenously introduced cAMP-GEFII may form a complex with endogenous Rim2.

Figure 9:
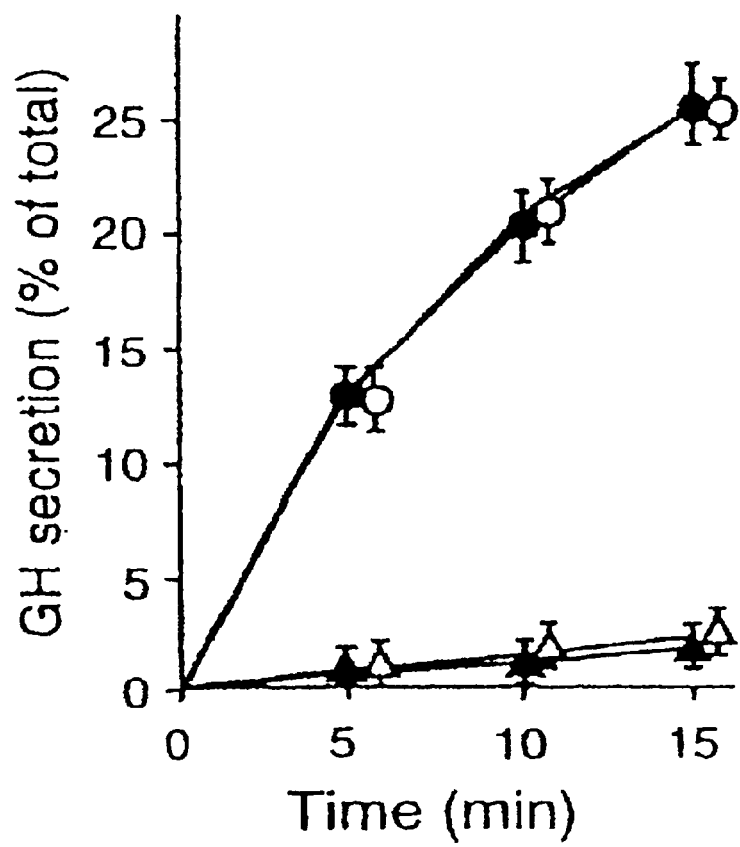
FIG. 9 is a graph showing the time course for high $K^+$-induced GH secretion from PC12 cells cotransfected with GH and cAMP-GEFII.
Figure 10:
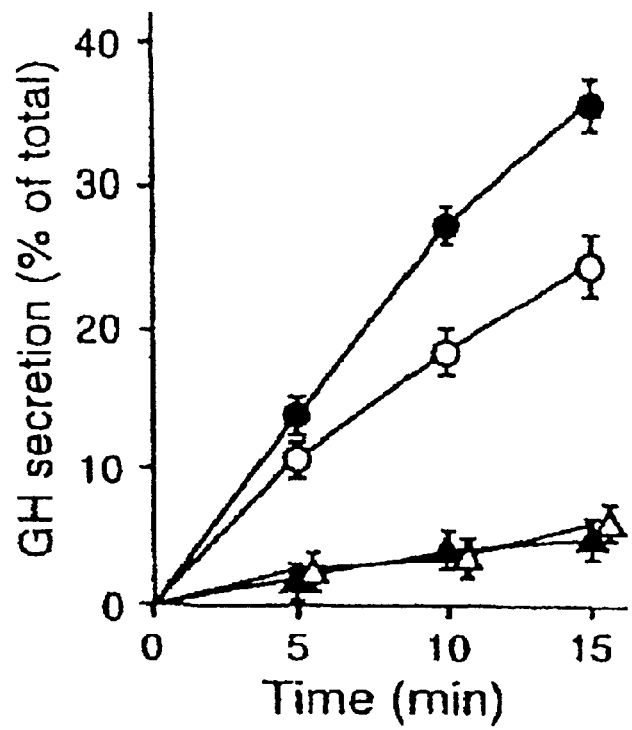
FIG. 10 is a graph showing the effect of forskolin on GH secretion from transfected PC cells.

FIG. 9 is a graph showing the time course of high $K^+$-induced GH secretion from PC12 cells cotransfected with GH and cAMP-GEFII. FIG. 10 is a graph showing the effect of forskolin on GH secretion from the transfected PC12 cells. Forskolin (50 μM) was added 10 min before the incubation with a low $K^+$ (4.7 mM) or high $K^+$ (60 mM) solution. The meaning of the symbols are as follows: For basal (low $K^+$-induced) secretion: cAMP-GEFII-transfectant (filled triangles); β-galactosidase-transfectant (control)(open circles); high $K^+$-induced secretion: cAMP-GEFII-transfectant (filled circles); β-galactosidase-transfectant (control)(open circles). The values represent the percent GH amounts released into the medium relative to the total cellular GH amounts.

In the cotransfected PC12 cells, as shown in FIG. 9, cAMP-GEFII did not alter $Ca^{2+}$-dependent (60 mM $K^+$) secretion of cotransfected GH, compared to the control, but significantly enhanced forskolin (50 μM)-induced, $Ca^{2+}$-dependent GH secretion (FIG. 10). Forskolin acts mainly on adenylate cyclase, serving to increase cAMP levels in the cells. cAMP-GEFII also enhanced 8-Br-cAMP (1 mM)-induced, $Ca^{2+}$-dependent GH secretion (cAMP-GEFII-transfectant, 34.9±1.3%; control, 25.1±1.8%, n=9, P<0.001).

Figure 11:
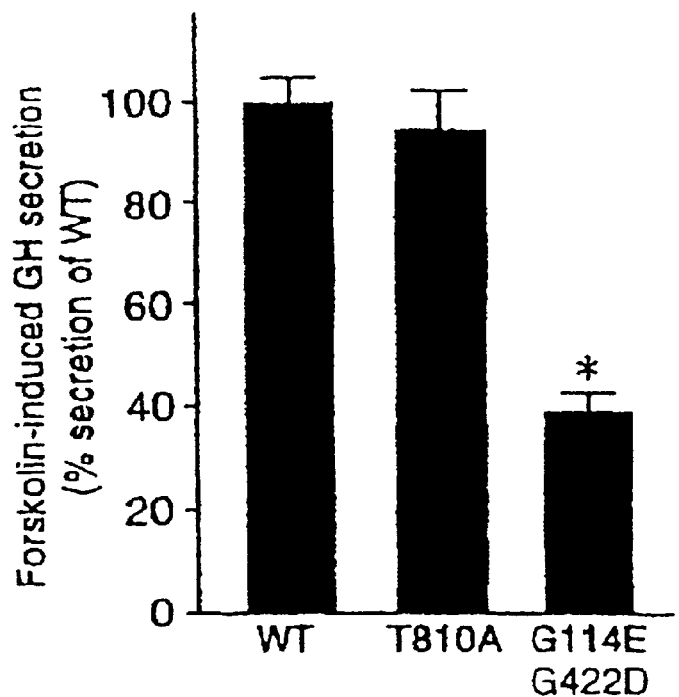
FIG. 11 is a graph showing forskolin-induced GH secretion from PC12 cells transfected with various mutant cAMP-GEFII.

FIG. 11 is a graph showing forskolin-induced GH secretion from PC12 cells transfected with various mutant cAMP-GEFII, in which the increment of forskolin (50 μM)-induced GH secretion (in the presence of high $K^+$) above the basal level during a 15-min incubation for each mutant cAMP-GEFII is expressed as percentage relative to the wild-type cAMP-GEFII (100%). In the figure: WT=wild-type cAMP-GEFII, T810A=mutant cAMP-GEFII (T810A); G114E, G422D=double mutant cAMP-GEFII (G114, G422D).

The forskolin-induced GH secretion was not affected in the mutant cAMP-GEFII (T810A) in which a potential PKA phosphorylation site is disrupted by substitution of one of its amino acids (FIG. 11). In addition, the forskolin-induced GH secretion in the mutant cAMP-GEFII (G114E, G422D) in which both of the cAMP binding sites are disputed was reduced to ~40% of that in the wild-type.

These results indicate that cAMP promotes $Ca^{2+}$-dependent GH secretion by binding to cAMP-GEFII, without involving its phosphorylation by PKA.

Figure 12:
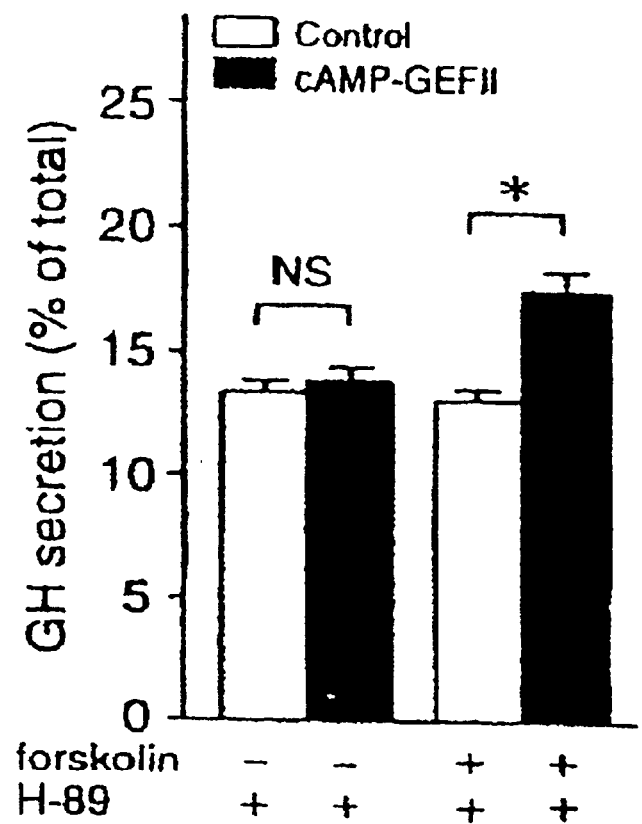
FIG. 12 is a graph showing the effect of H-89 on forskolin-induced GH secretion from PC12 cells transfected with cAMP-GEFII.

FIG. 12 is a graph showing the effect of H-89 on forskolin-induced GH secretion from cAMP-GEFII-transfected PC12 cells. H-89 (10 μM) was added to the incubation buffer 10 min before forskolin (50 μM) treatment. The treatment with H-89 (10 μM) reduced high $K^+$-induced GH secretion in both of the cAMP-GEFII-transfected and β-galactosidase-transfected PC12 cells. The data were obtained from 3–5 independent experiments (A–D). The values are means ± SEM (P<0.01).

Importantly, the forskolin-induced, $Ca2^+$-dependent GH secretion from the cAMP-GEFII-transfected PC12 cells treated with the PKA inhibitor H-89 was significantly higher than that from the control cells. This indicates that cAMP-GEFII mediates cAMP-dependent and PKA-independent exocytosis.

To ascertain the physiological relevance of cAMP-GEFII, the present inventors investigated the role of endogenous cAMP-GEFII in secretion. In insulin secretion from pancreatic β-cells, cAMP is proposed to stimulate exocytosis by PKA-dependent as well as PKA-independent mechanisms [M. Prentki, F. M. Matschinsky, Physiol. Rev. 67:1185 (1987)/P. M. Jones, S. J. Persaud, Endocrine. Rev. 19:429 (1998)].

In the high glucose condition of 16.7 mM, 8-Br-cAMP-induced insulin secretion from MIN6 cells treated with antisense oligonucleotides against cAMP-GEFII was significantly reduced (87.5±2.3% of the secretion from MIN6 cells treated with a control oligonucleotide, n=27, P<0.005) (See "Study of the Role of cAMP-GEFII in cAMP-dependent Exocytosis"), suggesting that cAMP-GEFII participates in cAMP-dependent exocytosis in native cells.

Rab3 is associated with the final step of exocytosis. The structurally-related proteins rabphilin3 [H. Shirataki et al., Mol. Cell. Biol. 13,2061 (1993)] and Rim1 both bind to Rab3A, suggesting that multiple Rab3A effectors could operate in triggering docking and fusion of the vesicles to the plasma membrane.

In the process toward the present invention, it was found that the cAMP sensor, cAMP-GEFII, mediates cAMP-induced, Ca²⁺-dependent exocytosis by interacting with a Rab3 effector Rim2.

In addition to its role in PKA phosphorylation of proteins associated with secretory processes, previous studies have suggested that cAMP may act directly on the exocytosis [G. Lonart, et al., Neuron 21:1141 (1998); E. Renstrom, et al., J. Physiol. 502:105(1997); K. Yoshimura et al., Biochim. Biophys. Acta 1402:171(1998)]. In pancreatic β-cells, too, PKA-dependent as well as PKA-independent stimulation of insulin release by cAMP has been proposed [E. Renstrom, et al., J. Physiol. 502:105 (1997)]. It is thought that cAMP probably directly stimulates amylase release in parotid acinar cells [G. Lonart, et al., Neuron 21:1141 (1998)]. In addition, a recent study suggests that cAMP enhances glutamate release in the brain partly by a direct action on the exocytotic machinery [G. Lonart, et al., Neuron 21,1141 (1998)].

However, while both rabphilin3 and Rim1 are ubiquitously expressed in most of the synapses in the brain[C. Li et al., Neuron 13:885 (1994)], cAMP-enhanced glutamate release occurs in synaptosomes from the CA3 region in the hippocampus, not from the CA1 region, a finding consistent with cAMP-GEFII and Rim1 being coexpressed predominantly in CA3.

Figure 13:
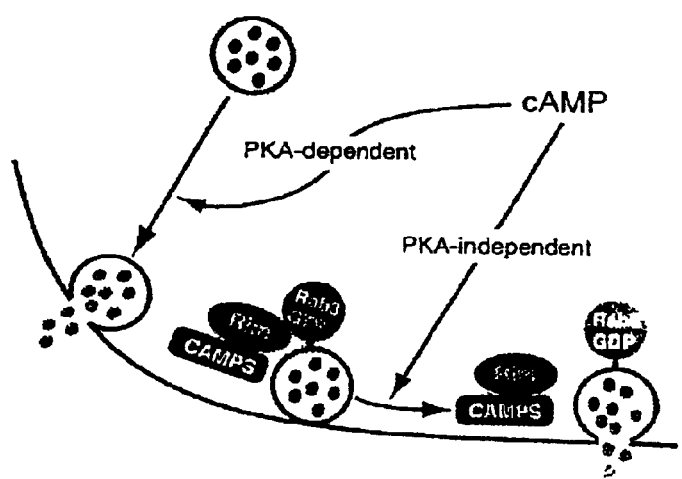
FIG. 13 is a schematic illustration showing a model for cAMP-dependent exocytosis.

Accordingly, it is considered that, in addition to PKA-dependent phosphorylation in the secretory processes, cAMP promotes regulated exocytosis in a PKA-independent manner by acting directly on a complex of cAMP-GEFII (a cAMP sensor) and Rim (a Rab3 effector) in some neurons and neuroendocrine and endocrine cells, as schematically illustrated in FIG. 13.

These findings indicates that Rim2 of the present invention also plays an important role in the regulation of exocytosis in neurons and endocrine cells.

EXAMPLES

The present invention will be described below in further detail by presenting specific procedures in the present invention with reference to an example.

<Sequencing of CAMPS (cAMP-GEFII) cDNA>

A plasmid cDNA library has been made from a mouse insulin-secreting cell line, MIN6, in the vector pVP16. A yeast two-hybrid bait vector was constructed in plasmid pBTM116 using a DNA fragment encoding partial rat SUR1 (amino acid residues 598–1003)(GenBank accession number L40624), a subunit of the pancreatic β-cell $K_{ATP}$ channel.

Yeast two-hybrid screen of the plasmid MIN6 cDNA library was performed as described in K. Kotake et al., J. -Biol. Chem. 272:29407 (1997). A prey clone encoding a partial CAMPS, a cAMP sensor, (residues 187–730) was isolated. A full-length mouse CAMPS cDNA was obtained from the λ MIN6 cDNA library [N. Inagaki et al., Proc. Natl. Acad. Sci. U.S.A. 91:2679(1994)]. The nucleotide sequence of mouse CAMPS (cAMP-GEFII) has been deposited in Genbank with the accession number of AB021132.

<Preparation and Test of GST fusion Protein> cAMP-A (amino acid residues 43–153), cAMP-B (amino acid residues 357–469), and rat PKA regulatory subunit (RI α)(full-length) were expressed as GST-fusion proteins using pGEX-4T-1 (Amersham-Pharmacia) and purified according to the manufacturer's instructions. cAMP binding assay was performed as described in R. A. Steiberg, et al., J. Biol. Chem. 262:2664(1987) with slight modifications.

Briefly, GST-fusion protein (1 μg) was incubated in binding buffer (200 μl) containing various concentrations of [³H]cAMP, 50 mM potassium phosphate buffer (pH 6.8), 150 mM NaCl, 1 mM EDTA, 5 mM 2-mercaptoethanol, and 0.5 mg/ml bovine serum albumin with or without 40 mM unlabeled cAMP for 2 hrs on ice.

<Identification of Interacting Molecules by YTH Method>

Yeast two-hybrid bait vector was constructed in plasmid pBTM116 using a full-length mouse cAMP-GEFII cDNA. A prey clone encoding a partial sequence of Rim2 (amino acid residues 53–863) was isolated from the plasmid MIN6 cDNA library. A full-length cDNA for Rim2 was obtained from the λ MIN6 cDNA library.

<Study on Interaction between Rim2 and cAMP-GEFII: I>

Rim2 (amino acid residues 538–863) was expressed as a GST fusion protein and purified according to the method described in "Preparation and Test of GST fusion Protein". A full-length cAMP-GEFII cDNA was subcloned into plasmid pFLAG-CMV-2 (Sigma). The resultant construct was transfected into COS-1 cells, using LipofectAMINE (Life Technologies). The lysate of the COS-1 cells was incubated with GST-Rim2 immobilized on glutathione beads for 2 hrs at 4° C. The complex thus obtained was washed with distilled water, separated by SDS-PAGE, and immunoblotted with an anti-FLAG M2 antibody (Sigma).

<Study on Interaction between Rim2 and cAMP-GEFII: II>

The lysate of MIN6 cells was incubated with GST-Rim2 and interaction between cAMP-GEFII and Rim2 was evaluated according to the method described in "Study on Interaction between Rim2 and cAMP-GEFII: I", using a IgG antibody raised against the C-terminus (amino acid residues 1001–1011, Gln-Met-Ser-His-Arg-Leu-Glu-Pro-Arg-Arg-Pro) (SEQ ID NO:5) of mouse cAMP-GEFII.

<Study on Interaction between Rim1 and cAMP-GEFII>

According to the method described in "Preparation and Test of GST fusion Protein", Rim1 partial sequence (530–806) was expressed as a GST fusion protein and then purified. The brain homogenate from three mice was incubated with GST-Rim1 immobilized on glutathione beads overnight at 4° C. cAMP-GEFII was detected as described in "Study on Interaction between Rim2 and cAMP-GEFII: II".

<Northern Blotting in Rat Tissues>

Northern Blotting was performed for various tissues of rat using, as probes, mouse cAMP-GEFII (nucleic acids 606–2237), rat Rim1 (1035–1491), and mouse Rim2 (586–1490) cDNA <In situ Hybridization in Mouse Brain>

In situ hybridization in mouse brain was performed as described in J. Tanaka, M. Murate, C. Z. Wang, S. Seino, T. Iwanaga, Arch. Histol. Cytol. 59:485 (1996).

Antisense oligonucleotide probes (45 mer) used for mouse cAMP-GEFII and Rim2 correspond to the regions of the nucleic acids 2746–2790 and 1376–1420, respectively.

For the antisense oligonucleotide for Rim1, Rim1 cDNA was partially cloned from mouse brain: the probe used in this was 5'-ttgcgctcactcttctggcctcccttgccattctgctctgaaagc-3' (SEQ ID NO:3).

<Study on Interaction between Rim2 and Rab3A>

According to the method described in "Identification of Interacting molecules by YTH Method", the full-length cDNA's for wild type mouse Rab3A and constitutively active bovine Rab3A (Q81L) were cloned into the yeast bait vector pBTM116.

The nucleotide sequence of zinc finger domains of bovine rabphilin3 (amino acid residues 1–283), rat Rim1 (amino acid residues 1–204) and mouse Rim2 (amino acid residues 1–345 were cloned into the prey vector pVP16. Liquid culture assay of ε-galactosidase activities was performed according to the manufacturer's instructions (Clontech). The activity values were obtained from 3 independent clones for each transformant and normalized by cell numbers determined as $OD_{600}$.

Lipid-modified Rab3A was purified from the membrane fraction of Sf9 cells expressing Rab3A. Rat Rim1 (amino acid residues 1–204) and mouse Rim2 (amino acid residues 1–345) were expressed as GST fusion proteins and purified. The GTP γS- or GDP βS-bound form of Rab3A was incubated for 90 min at 4° C. with GST-Rim1, or GST-Rim2 (30 pmol for each) immobilized on glutathione beads in reaction buffer. Rab3A was detected by immunoblotting with anti-Rab3A antibody.

<Study on GH Secretion from Transfected PC12 Cells>

GH secretion from transfected PC12 cells was performed as described in K. Korake et al., J. Biol. Chem., 272:29407 (1997). Expression plasmid vectors (pSR α) for wild-type cAMP-GEFII, mutant cAMP-GEFII (T810A), and the double mutant cAMP-GEFII (G114E, G422D) were prepared. As a control, β-galactosidase (β-gal) was used. PC cells were transfected with GH expression vector (pXGH5: Nichols Institute) plus each vector described above, using LipofectAMINE.

PC12 cell were incubated with a low $K^{30}$ (4.7 mM) or high $K^+$ (60 mM) solution, in the presence or absence of forskolin (50 μM) or 8-bromoadenosine 3',5' cyclic monophosphate (8-Br-cAMP)(1 mM). Forskolin or 8-Br-cAMP was added 10 min before the incubation with a low or high $K^+$ solution. In some experiments, the PKA inhibitor H-89 (10 μM) was added 10 min before forskolin stimulation.

<Study of the Role of cAMP-GEFII in cAMP-dependent Exocytosis>

To interfere with the synthesis of cAMP-GEFII in MIN6 cells, antisense phosphorothioate-substituted oligoDNA (16 mer) against mouse cAMP-GEFII (the region corresponding to nucleic acids 104–119) and control oligoDNA (5'-acctacgtgactacgt-3') (SEQ ID NO:4) were synthesized (BIOGNOSTIK).

MIN6 cells were treated with 4 μM of the antisense oligoDNA or control oligoDNA 24 hours before insulin secretion experiments. The efficacy of antisense oligoDNA was evaluated by immunoblot analysis of the antisense oligoDNA-treated MIN6 cells over-expressing cAMP-GEFII by transient transfection, using anti-cAMP-GEFII antibody. The level of cAMP-GEFII was markedly lowered in the antisense oligoDNA-treated MIN6 cells. Insulin secretory response to 8-Br-cAMP (1 mM) of these MIN6 cells was assessed in the presence of high glucose (16.7 mM). Five separate experiments were performed, in which insulin was measured as described in T. Gonoi et al., J. Biol. Chem. 269:16989 (1994).

SEQUENCE LISTING

```
<151> PRIOR FILING DATE: 1999-10-08<160>  5

<210> SEQ ID NO 1
<211> LENGTH: 1590
<212> TYPE: PRT
<213> ORGANISM: Mus musculus

<400> SEQUENCE: 1

Met Ser Ala Pro Leu Gly Pro Arg Gly Arg Pro Ala Pro Thr Pro Ala
1               5                   10                  15

Ala Ser Gln Pro Pro Gln Pro Glu Met Pro Asp Leu Ser His Leu
            20                  25                  30

Thr Glu Glu Glu Arg Lys Ile Ile Leu Ala Val Met Asp Arg Gln Lys
            35                  40                  45

Lys Glu Glu Glu Lys Glu Gln Ser Val Leu Lys Ile Lys Glu Glu His
        50                  55                  60

Lys Ala Gln Pro Thr Gln Trp Phe Pro Phe Ser Gly Ile Thr Glu Leu
65                  70                  75                  80

Val Asn Asn Val Leu Gln Pro Gln Gln Lys Gln Pro Asn Glu Lys Glu
                85                  90                  95

Pro Gln Thr Lys Leu His Gln Gln Phe Glu Met Tyr Lys Glu Gln Val
            100                 105                 110

Lys Lys Met Gly Glu Glu Ser Gln Gln Gln Gln Glu Gln Lys Gly Asp
        115                 120                 125

Ala Pro Thr Cys Gly Ile Cys His Lys Thr Lys Phe Ala Asp Gly Cys
    130                 135                 140

Gly His Asn Cys Ser Tyr Cys Gln Thr Lys Phe Cys Ala Arg Cys Gly
145                 150                 155                 160

Gly Arg Val Ser Leu Arg Ser Asn Lys Val Met Trp Val Cys Asn Leu
                165                 170                 175

Cys Arg Lys Gln Gln Glu Ile Leu Thr Lys Ser Gly Ala Trp Phe Tyr
            180                 185                 190
```

-continued

```
Asn Ser Gly Ser Asn Thr Leu Gln Gln Pro Asp Gln Lys Val Pro Arg
        195                 200                 205

Gly Leu Arg Asn Glu Glu Ala Pro Gln Glu Lys Lys Ala Lys Leu His
    210                 215                 220

Glu Gln Pro Gln Phe Gln Gly Ala Pro Gly Asp Leu Ser Val Pro Ala
225                 230                 235                 240

Val Glu Lys Gly Arg Ala His Gly Leu Thr Arg Gln Asp Thr Ile Lys
                245                 250                 255

Asn Gly Ser Gly Val Lys His Gln Ile Ala Ser Asp Met Pro Ser Asp
            260                 265                 270

Arg Lys Arg Ser Pro Ser Val Ser Arg Asp Gln Asn Arg Arg Tyr Glu
        275                 280                 285

Gln Ser Glu Glu Arg Glu Asp Tyr Ser Gln Tyr Val Pro Ser Asp Gly
    290                 295                 300

Thr Met Pro Arg Ser Pro Ser Asp Tyr Ala Asp Arg Arg Ser Gln Arg
305                 310                 315                 320

Glu Pro Gln Phe Tyr Glu Glu Pro Gly His Leu Asn Tyr Arg Asp Ser
                325                 330                 335

Asn Arg Arg Gly His Arg His Ser Lys Glu Tyr Ile Val Asp Asp Glu
            340                 345                 350

Asp Val Glu Ser Arg Asp Glu Tyr Glu Arg Gln Arg Arg Glu Glu Glu
        355                 360                 365

Tyr Gln Ala Arg Tyr Arg Ser Asp Pro Asn Leu Ala Arg Tyr Pro Val
    370                 375                 380

Lys Pro Gln Pro Tyr Glu Glu Gln Met Arg Ile His Ala Glu Val Ser
385                 390                 395                 400

Arg Ala Arg His Glu Arg Arg His Ser Asp Val Ser Leu Ala Asn Ala
                405                 410                 415

Glu Leu Glu Asp Ser Arg Ile Ser Leu Leu Arg Met Asp Arg Pro Ser
            420                 425                 430

Arg Gln Arg Ser Val Ser Glu Arg Arg Ala Ala Met Glu Asn Gln Arg
        435                 440                 445

Ser Tyr Ser Met Glu Arg Thr Arg Glu Ala Gln Gly Gln Ser Ser Tyr
    450                 455                 460

Pro Gln Arg Thr Ser Asn His Ser Pro Thr Pro Arg Arg Ser Pro
465                 470                 475                 480

Ile Pro Leu Asp Arg Pro Asp Met Arg Arg Ala Asp Ser Leu Arg Lys
                485                 490                 495

Gln His His Leu Asp Pro Ser Ser Ala Val Arg Lys Thr Lys Arg Glu
            500                 505                 510

Lys Met Glu Thr Met Leu Arg Asn Asp Ser Leu Ser Ser Asp Gln Ser
        515                 520                 525

Glu Ser Val Arg Pro Pro Pro Arg Pro His Lys Ser Lys Lys Gly
    530                 535                 540

Gly Lys Met Arg Gln Val Ser Leu Ser Ser Glu Glu Leu Ala
545                 550                 555                 560

Ser Thr Pro Glu Tyr Thr Ser Cys Asp Asp Val Glu Leu Glu Ser Glu
                565                 570                 575

Ser Val Ser Glu Lys Gly Asp Ser Gln Lys Gly Lys Arg Lys Thr Ser
            580                 585                 590

Glu Gln Gly Val Leu Ser Asp Ser Asn Thr Arg Ser Glu Arg Gln Lys
        595                 600                 605
```

-continued

Lys Arg Met Tyr Tyr Gly Gly His Ser Leu Glu Glu Asp Leu Glu Trp
610                615                620

Ser Glu Pro Gln Ile Lys Asp Ser Gly Val Asp Thr Cys Ser Ser Thr
625                630                635                640

Thr Leu Asn Glu Glu His Ser His Ser Asp Lys His Pro Val Thr Trp
                645                650                655

Gln Pro Ser Lys Asp Gly Asp Arg Leu Ile Gly Arg Ile Leu Leu Asn
                660                665                670

Lys Arg Leu Lys Asp Gly Ser Val Pro Arg Asp Ser Gly Ala Met Leu
                675                680                685

Gly Leu Lys Val Val Gly Gly Lys Met Thr Glu Ser Gly Arg Leu Cys
690                695                700

Ala Phe Ile Thr Lys Val Lys Lys Gly Ser Leu Ala Asp Thr Val Gly
705                710                715                720

His Leu Arg Pro Gly Asp Glu Val Leu Glu Trp Asn Gly Arg Leu Leu
                725                730                735

Gln Gly Ala Thr Phe Glu Glu Val Tyr Asn Ile Ile Leu Glu Ser Lys
                740                745                750

Pro Glu Pro Gln Val Glu Leu Val Val Ser Arg Pro Ile Gly Asp Ile
                755                760                765

Pro Arg Ile Pro Asp Ser Thr His Ala Gln Leu Glu Ser Ser Ser Ser
770                775                780

Ser Phe Glu Ser Gln Lys Met Asp Arg Pro Ser Ile Ser Val Thr Ser
785                790                795                800

Pro Met Ser Pro Gly Met Leu Arg Asp Val Pro Gln Phe Leu Ser Gly
                805                810                815

Gln Leu Ser Ile Lys Leu Trp Phe Asp Lys Val Gly His Gln Leu Ile
                820                825                830

Val Thr Ile Leu Gly Ala Lys Asp Leu Pro Ser Arg Glu Asp Gly Arg
                835                840                845

Pro Arg Asn Pro Tyr Val Lys Ile Tyr Phe Leu Pro Asp Arg Ser Asp
850                855                860

Lys Asn Lys Arg Arg Thr Lys Thr Val Lys Thr Leu Glu Pro Lys
865                870                875                880

Trp Asn Gln Thr Phe Ile Tyr Ser Pro Val His Arg Arg Glu Phe Arg
                885                890                895

Glu Arg Met Leu Glu Ile Thr Leu Trp Asp Gln Ala Arg Val Arg Glu
                900                905                910

Glu Glu Ser Glu Phe Leu Gly Glu Ile Leu Ile Glu Leu Glu Thr Ala
                915                920                925

Leu Leu Asp Asp Glu Pro His Trp Tyr Lys Leu Gln Thr His Asp Val
930                935                940

Ser Ser Leu Pro Leu Pro Arg Pro Ser Pro Tyr Leu Pro Arg Arg Gln
945                950                955                960

Leu His Gly Glu Ser Pro Thr Arg Arg Leu Gln Arg Ser Lys Arg Ile
                965                970                975

Ser Asp Ser Glu Val Ser Asp Tyr Asp Cys Glu Asp Gly Val Gly Val
                980                985                990

Val Ser Asp Tyr Arg His Asn Gly Arg Asp Leu Gln Ser Ser Thr Leu
                995                1000                1005

Ser Val Pro Glu Gln Val Met Ser Ser Asn His Cys Ser Pro Ser
     1010                1015                1020

Gly Ser Pro His Arg Val Asp Val Ile Gly Arg Thr Arg Ser Trp

-continued

```
             1025                1030                1035
Ser Pro Ser Ala Pro Pro Gln Arg Asn Val Glu Gln Gly His
    1040                1045                1050
Arg Gly Thr Arg Ala Thr Gly His Tyr Asn Thr Ile Ser Arg Met
    1055                1060                1065
Asp Arg His Arg Val Met Asp Asp His Tyr Ser Ser Asp Arg Asp
    1070                1075                1080
Arg Asp Cys Glu Ala Ala Asp Arg Gln Pro Tyr His Arg Ser Arg
    1085                1090                1095
Ser Thr Glu Gln Arg Pro Leu Leu Glu Arg Thr Thr Arg Ser
    1100                1105                1110
Arg Ser Ser Glu Arg Pro Asp Thr Asn Leu Met Arg Ser Met Pro
    1115                1120                1125
Ser Leu Met Thr Gly Arg Ser Ala Pro Pro Ser Pro Ala Leu Ser
    1130                1135                1140
Arg Ser His Pro Arg Thr Gly Ser Val Gln Thr Ser Pro Ser Ser
    1145                1150                1155
Thr Pro Gly Thr Gly Arg Arg Gly Arg Gln Leu Pro Gln Leu Pro
    1160                1165                1170
Pro Lys Gly Thr Leu Glu Arg Ser Ala Met Asp Ile Glu Glu Arg
    1175                1180                1185
Asn Arg Gln Met Lys Leu Asn Lys Tyr Lys Gln Val Ala Gly Ser
    1190                1195                1200
Asp Pro Arg Leu Glu Gln Asp Tyr His Ser Lys Tyr Arg Ser Gly
    1205                1210                1215
Trp Asp Pro His Arg Gly Ala Asp Thr Val Ser Thr Lys Ser Ser
    1220                1225                1230
Asp Ser Asp Val Ser Asp Val Ser Ala Val Ser Arg Thr Ser Ser
    1235                1240                1245
Ala Ser Arg Phe Ser Ser Thr Ser Tyr Met Ser Val Gln Ser Glu
    1250                1255                1260
Arg Pro Arg Gly Asn Arg Lys Ile Ser Val Phe Thr Ser Lys Met
    1265                1270                1275
Gln Asn Arg Gln Met Gly Val Ser Gly Lys Asn Leu Thr Lys Ser
    1280                1285                1290
Thr Ser Ile Ser Gly Asp Met Cys Ser Leu Glu Lys Asn Asp Gly
    1295                1300                1305
Ser Gln Ser Asp Thr Ala Val Gly Ala Leu Gly Thr Ser Gly Lys
    1310                1315                1320
Lys Arg Arg Ser Ser Ile Gly Ala Lys Met Val Ala Ile Val Gly
    1325                1330                1335
Leu Ser Arg Lys Ser Arg Ser Ala Ser Gln Leu Ser Gln Thr Glu
    1340                1345                1350
Gly Gly Gly Lys Lys Leu Arg Ser Thr Val Gln Arg Ser Thr Glu
    1355                1360                1365
Thr Gly Leu Ala Val Glu Met Arg Asn Trp Met Thr Arg Gln Ala
    1370                1375                1380
Ser Arg Glu Ser Thr Asp Gly Ser Met Asn Ser Tyr Ser Ser Glu
    1385                1390                1395
Gly Asn Leu Ile Phe Pro Gly Val Arg Leu Ala Ser Asp Ser Gln
    1400                1405                1410
Phe Ser Asp Phe Leu Asp Gly Leu Gly Pro Ala Gln Leu Val Gly
    1415                1420                1425
```

```
Arg Gln  Thr Leu Ala Thr Pro  Ala Met Gly Asp Ile  Gln Val Gly
    1430             1435                 1440

Met Met  Asp Lys Lys Gly Gln  Leu Glu Val Glu Ile  Ile Arg Ala
    1445             1450                 1455

Arg Gly  Leu Val Val Lys Pro  Gly Ser Lys Thr Leu  Pro Ala Pro
    1460             1465                 1470

Tyr Val  Lys Val Tyr Leu Leu  Asp Asn Gly Val Cys  Ile Ala Lys
    1475             1480                 1485

Lys Lys  Thr Lys Val Ala Arg  Lys Thr Leu Glu Pro  Leu Tyr Gln
    1490             1495                 1500

Gln Leu  Leu Ser Phe Glu Glu  Ser Pro Gln Gly Arg  Val Leu Gln
    1505             1510                 1515

Ile Ile  Val Trp Gly Asp Tyr  Gly Arg Met Asp His  Lys Ser Phe
    1520             1525                 1530

Met Gly  Val Ala Gln Ile Leu  Leu Asp Glu Leu Glu  Leu Ser Asn
    1535             1540                 1545

Met Val  Ile Gly Trp Phe Lys  Leu Phe Pro Pro Ser  Ser Leu Val
    1550             1555                 1560

Asp Pro  Thr Ser Ala Pro Leu  Thr Arg Arg Ala Ser  Gln Ser Ser
    1565             1570                 1575

Leu Glu  Ser Ser Thr Gly Pro  Ser Tyr Ser Arg Ser
    1580             1585                 1590

<210> SEQ ID NO 2
<211> LENGTH: 4980
<212> TYPE: DNA
<213> ORGANISM: Mus musculus

<400> SEQUENCE: 2
gcttccctag ggtggttcgg ctccgccaaa catgtcggct ccgctcgggc cccggggccg      60
cccggctccc accccggcgg cctctcaacc tcctccgcag cccgagatgc cggacctcag     120
ccacctcacg gaagaggaga ggaaaatcat cctggctgtc atggatcgtc agaagaaaga     180
agaggagaag gagcagtccg tgctcaagat caaagaagaa cacaaagcac aaccgacaca     240
gtggtttccc tttagtggga tcactgaact ggtaaataac gttctgcagc cccagcaaaa     300
acaacccaat gagaaggagc cccagacaaa gctgcaccaa caatttgaaa tgtataagga     360
gcaagtcaag aagatgggag aggaatcgca gcagcagcaa gagcagaagg gtgatgcccc     420
gacctgtggc atctgccaca agacaaaatt tgcagatgga tgcggccata attgttccta     480
ttgccaaacc aagttctgtg ctcgatgtgg aggtcgagtg tctttacgct caaacaaggt     540
tatgtgggtg tgtaatttgt gccgaaaaca acaagaaatc ctcactaaat caggagcatg     600
gttttataat agtgggtcta acacactgca gcaacctgat caaaaggttc ctcgagggct     660
tcgaaatgag gaagcccctc aggagaagaa agcaaaacta cacgagcagc cccagttcca     720
aggagcccca ggtgacttat cagtacctgc agttgagaaa ggccgagctc atgggctcac     780
aagacaggat actattaaaa atggatcagg agtgaagcac cagattgcca gtgacatgcc     840
ttcagacaga aaacgaagtc catcagtgtc cagggatcaa aatcgaagat acgagcaaag     900
tgaagaaaga gaggactact cacagtatgt tccttcagat ggtacaatgc caagatctcc     960
ttcggattat gctgatagac gatctcagcg tgagcctcaa tttatgaagg aacctggtca    1020
tttaaattac aggattcta acaggagagg ccatagacat tccaaagagt atattgtgga    1080
tgatgaagat gtggagagca gagatgaata tgaaagacaa aggagagagg aggaatacca    1140
```

```
ggcacgctac agaagtgatc caaatctggc ccggtatccc gtaaagccac aaccctacga   1200
agaacaaatg cgcatccacg ctgaggtgtc cagggcacga catgagagaa ggcacagtga   1260
tgtttctttg gcaaacgctg aactagaaga ttccaggatt tctctgctaa ggatggatag   1320
accatcaagg caaagatctg tatctgaacg tagagctgca atggaaaacc aacgatcgta   1380
ttcaatggaa agaactcgag aggctcaggg acaaagttct tatccacaaa ggacctcaaa   1440
tcatagtcct cccacccctc ggcggagccc tataccgctt gatagaccag acatgaggcg   1500
cgctgactcc ctacggaaac agcaccactt agatcccagc tctgctgtga ggaaaacgaa   1560
gcgagaaaaa atggaaacca tgttaaggaa tgattctttg agttcagacc agtccgagtc   1620
agtgaggccg cccccaccaa ggcctcataa atccaagaaa ggaggtaaaa tgcgccaggt   1680
ttcactgagc agctcggagg aggagctggc atccacacct gagtatacaa gctgtgatga   1740
tgtggagctg gaaagcgaga gtgtgagtga aaaggggac agtcaaaagg gaaaagaaa    1800 aactagtgag cagggagttt tgtcggattc taacaccagg tctgagagac aaaagaaaag   1860
gatgtactat ggtggccact ctttggaaga ggatttggaa tggtctgagc ctcagattaa   1920
ggactctggg gtagatacct gtagtagcac aaccettaac gaggagcata gccatagtga   1980
taagcaccct gtgacctggc agccatccaa agatggagat cgcctaattg gtcgtatttt   2040
attaaataag cgtttaaaag atgggagtgt acctcgagac tcaggagcaa tgctgggctt   2100
aaaggttgta ggaggaaaga tgactgaatc aggtcgactt tgtgcattta ttaccaaagt   2160
aaaaaaagga agtttagctg atactgtagg acatcttaga ccaggtgatg aagtcttgga   2220
atggaatggg aggctattgc aaggagccac atttgaggaa gtttacaaca ttattctaga   2280
atccaaacct gaaccacaag ttgagcttgt tgtttcaagg ccaattggag atattcctag   2340
aatacctgat agcacgcatg cacaactgga atccagttct agctcatttg aatctcaaaa   2400 aatgaccgt ccttctatat ccgttacctc acccatgagt cctggcatgc tgagggatgt    2460
cccgcagttc ttatctggac agctttcaat aaaactatgg tttgacaagg ttggtcacca   2520
gttgatagtt acaattttgg gagcaaagga tctcccttcc agggaagatg ggaggccaag   2580
gaatccttat gttaagattt acttccttcc agatagaagt gataaaaata agagaagaac   2640
aaaaacagtc aagaaaactt tggaacccaa atggaaccag actttcatt attctcctgt    2700 ccaccgaaga gaattccgtg aacgaatgct ggaaattacc ctttgggatc aagctagagt   2760
tcgagaagaa gagagcgaat tcttaggaga gattttaatt gaattggaaa cagctttgct   2820
agatgatgag ccgcactggt ataagctgca gacccatgat gtctcctcat tgccactccc   2880
tcgcccttcc ccatatctgc cccggaggca gctccatgga gagagcccaa cgcgcaggct   2940
gcaaaggtcg aagagaataa gtgacagtga agtgtctgac tacgactgcg aggatggcgt   3000
gggagtagtg tcagattatc gacacaatgg ccgcgatctt caaagctcca cgttgtcggt   3060
gccagaacaa gtcatgtcat caaatcattg ctcaccatca gggtctcctc atcgagtaga   3120
tgttatagga aggacaaggt catggtcgcc tagtgcccct cctcctcaaa ggaatgtgga   3180 acagggcac cgagggacac gtgctactgg ccattacaac acaattagcc gaatggatag    3240
acaccgtgtc atggatgacc actactcttc agatagagac agggattgtg aagcagcaga   3300
tagacagcca tatcacagat ccagatcaac agaacaacgg cctctcctag agcggaccac   3360
cacccgctcc agatcctctg aacgtcctga tacaaacctc atgaggtcga tgccttcatt   3420
aatgactgga agatctgccc ctccttcacc tgccttatcg aggtctcacc ctcgtaccgg   3480
```

-continued

```
gtctgtccag acaagcccat caagtactcc gggaacagga cgaagggcc gacagcttcc   3540 acagcttcca ccaaagggaa cattggagag aagtgctatg gatatagagg agagaaatcg   3600
ccaaatgaaa cttaacaaat acaaacaggt agccggatca gaccccagac tggagcaaga   3660
ttaccattcg aagtatcgct caggatggga tccacataga ggggcagata ctgtttccac   3720
taaatcctcg gacagtgatg taagtgatgt atctgcggtt tcaaggacta gtagtgcttc   3780
tcgtttcagc agcacaagct acatgtccgt ccaatcagag cggccgagag gaaacaggaa   3840
aatcagtgtc tttacatcca aaatgcaaaa cagacagatg ggcgtgtcgg ggaagaactt   3900
gaccaaaagc accagcatca gtggagacat gtgctcactg gagaagaatg acggcagcca   3960
gtccgacact gcagtgggcg ccctgggtac cagtggcaag aagcggcgat ctagcattgg   4020
ggccaaaatg gtagctattg ttggtctctc acggaaaagt cgcagtgcct ctcaactcag   4080
ccaaaccgaa ggaggaggta aaaagctacg gagcactgtt cagagaagca cggagaccgg   4140
gctagcagtg gagatgagga actggatgac ccgccaggcc agccgggaat ccacagatgg   4200
cagcatgaac agctatagct cggaaggaaa tctgatcttc cctggggtcc gcctggcctc   4260
tgacagccag ttcagtgatt tcctggatgg cctgggccct gctcagctag tgggacgcca   4320
gaccctggct actcctgcaa tgggtgacat tcagtgggga atgatggata aaagggaca   4380 gctggaggta gaaatcatcc gggcgcgcgg ccttgtggta aaaccaggtt ccaagacact   4440
gccagcaccg tatgtcaagg tgtatctgtt agacaacgga gtctgcatag ccaaaaagaa   4500
aaccaaggtg gcgagaaaga ccctggagcc cctgtaccag cagctcttgt ccttcgagga   4560
gagcccccag gggagggtgt tacagatcat tgtctgggga gattatggtc gtatggatca   4620
caaatccttt atgggagtgg cccagatact cttagatgaa ctggaactat ccaacatggt   4680
gattggatgg ttcaaactct cccctccttc ctccctagta gatccaacct cggcacctct   4740
gacaagaaga gcttcccaat cgtctctgga aagttctacc ggaccttctt actctcgttc   4800
atagcaacta taaaactgtt gtcacaacaa ccagcgatac aaaaaccaga agaaaacgca   4860
caggtggaag cccctggtaa cactgcatgc ttgatgttgt gtctacagag cccacgtcta   4920
gggataccaa gcagtcctgt gttctcagag gaagtcgtac acattgtgcc ctagcaaagg   4980
```

<210> SEQ ID NO 3
<211> LENGTH: 45
<212> TYPE: DNA
<213> ORGANISM: Mus musculus

<400> SEQUENCE: 3

```
ttgcgctcac tcttctggcc tcccttgcca ttctgctctg aaagc           45
```

<210> SEQ ID NO 4
<211> LENGTH: 16
<212> TYPE: DNA
<213> ORGANISM: Mus musculus

<400> SEQUENCE: 4

```
acctacgtga ctacgt                                            16
```

<210> SEQ ID NO 5
<211> LENGTH: 11

```
-continued

<212> TYPE: PRT
<213> ORGANISM: Mus musculus

<400> SEQUENCE: 5

Gln Met Ser His Arg Leu Glu Pro Arg Pro
1               5                   10
```

What is claimed is:

1. An isolated protein having the amino acid sequence set forth in SEQ ID NO: 1.

2. An isolated protein having an amino acid sequence with from one to ten amino acids deleted, substituted, inserted or added relative to the amino acid sequence as set forth in SEQ ID NO: 1 and which interacts with GDP/GTP exchange factor II.

* * * * *